US009969802B2

(12) United States Patent
Ebinuma et al.

(10) Patent No.: US 9,969,802 B2
(45) Date of Patent: May 15, 2018

(54) METHOD FOR DETECTING MALIGNANT TUMOR CELLS

(75) Inventors: Hiroyuki Ebinuma, Ryugasaki (JP); Kohei Takubo, Ryugasaki (JP); Isamu Fukamachi, Ryugasaki (JP); Saishu Yoshida, Ryugasaki (JP); Hideaki Bujo, Chiba (JP); Chiaki Nakaseko, Chiba (JP); Yasushi Saito, Chiba (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 13 days.

(21) Appl. No.: 13/810,377

(22) PCT Filed: Jul. 15, 2011

(86) PCT No.: PCT/JP2011/066276
§ 371 (c)(1),
(2), (4) Date: Jan. 15, 2013

(87) PCT Pub. No.: WO2012/008594
PCT Pub. Date: Jan. 19, 2012

(65) Prior Publication Data
US 2013/0115229 A1 May 9, 2013

(30) Foreign Application Priority Data
Jul. 15, 2010 (JP) .................................. 2010-161037

(51) Int. Cl.
C07K 16/28 (2006.01)
G01N 33/574 (2006.01)
C07K 16/30 (2006.01)
G01N 33/92 (2006.01)

(52) U.S. Cl.
CPC .............. C07K 16/28 (2013.01); C07K 16/30 (2013.01); G01N 33/57492 (2013.01); G01N 33/92 (2013.01)

(58) Field of Classification Search
None
See application file for complete search history.

(56) References Cited

U.S. PATENT DOCUMENTS

| | | | |
|---|---|---|---|
| 5,665,872 A | 9/1997 | Saito et al. | |
| 6,355,623 B2 * | 3/2002 | Seidman et al. | 514/45 |
| 2003/0105000 A1 * | 6/2003 | Pero et al. | 514/12 |
| 2003/0198972 A1 * | 10/2003 | Erlander | C12Q 1/6886 435/6.11 |
| 2011/0091993 A1 | 4/2011 | Matsuo et al. | |
| 2011/0177610 A1 | 7/2011 | Matsuo et al. | |
| 2013/0029363 A1 | 1/2013 | Ebinuma et al. | |

FOREIGN PATENT DOCUMENTS

| | | |
|---|---|---|
| EP | 2 515 144 | 10/2012 |
| JP | 9 163988 | 6/1997 |
| WO | 2008 155891 | 12/2008 |
| WO | 2009 116268 | 9/2009 |

OTHER PUBLICATIONS

Rudikoff et al. (PNAS USA, 1982, 79: 1979-1983).*
Coleman et al. (Research in Immunology, 1994; 145(1): 33-36).*
Skolnick et al. (TIBTECH 18:34-39, 2000).*
Ibragimova and Wade (Biophysical Journal, Oct. 1999, vol. 77, pp. 2191-2198).*
Evers et al. (Annals of NY Acad. Sci. Sep. 1994 733: 393-406).*
Adam et al. (J. Biol. Chem. Feb. 21, 2003, 278(8): 6482-6489).*
U.S. Appl. No. 14/116,683, filed Nov. 8, 2013, Takubo, et al.
Extended European Search Report dated Jan. 31, 2014, in European Patent Application No. 11806924.4.
Paul J. Adam, et al., "Comprehensive proteomic analysis of breast cancer cell membranes reveals unique proteins with potential roles in clinical cancer", JBC Papers in Press, XP-002409464, Dec. 10, 2002, pp. 1-60.
Masahiro Takeuchi, et al., "LR11 Is a Novel Surface Marker for Normal Leukocytes and Leukemia Cells", Blood, vol. 116, XP-055096242, Nov. 19, 2010, (English Abstract 4834) 5 pages.
Christopher J. Shepherd, et al., "Expression profiling of CD133+ and CD133-epithelial cells from human prostate", The Prostate, Wiley-Liss, Inc., New York, vol. 68, No. 9, XP-002558897,Jun. 1, 2008, pp. 1007-1024.
Marie Ravoet, et al., "Molecular profiling of CD3-CD4+ T cells from patients with the lymphocytic variant of hypereosinophilic syndrome reveals targeting of growth control pathways", Blood, The American Society of Hematology, vol. 114, No. 14, XP-002562285, Oct. 1, 2009, pp. 2969-2983.
Hirayama, S., et al., "Differential Expression of LR11 during Proliferation and Differentiation of Cultured Neuroblastoma Cells," Biochemical and Biophical Research Communications, vol. 275, No. 2, pp. 365-373, (Jul. 23, 2000).
Hampe, W., et al., "Ectodomain shedding, translocation and synthesis of SorLA are stimulated by its ligand head activator," Journal of Cell Science, vol. 113, No. 24, pp. 4475-4485, (Nov. 16, 2000).
Gutekunst, C., et al., "Stigmoid Bodies Contain Type I Receptor Proteins SorLA/LR11 and Sortilin: New Prespectives on Their Function," The Journal of Histochemistry & Cytochemistry, vol. 51, No. 6, pp. 841-852, (2003).
Yamazaki, H., et al., "Elements of Neural Adhesion Molecules and a Yeast Vacuolar Protein Sorting Receptor Are Present in a Novel Mammalian Low Density Lipoprotein Receptor Family Member," The Journal of Biological Chemistry, vol. 271, No. 40, pp. 24761-24768, (Oct. 4, 1996).
Kanaki, T., et al., "Expression of LR11, a Mosaic LDL Receptor Family Member, Is Markedly Increased in Atherosclerotic Lesions," Arterioscler Thromb Vasc Biol., vol. 19, pp. 2687-2695, (1999).

(Continued)

*Primary Examiner* — Peter J Reddig
(74) *Attorney, Agent, or Firm* — Oblon, McClelland, Maier & Neustadt, L.L.P.

(57) ABSTRACT

Provided is a detection method for a malignant tumor cell, including measuring a protein marker expressed on a malignant tumor cell surface. The detection method for a malignant tumor cell includes measuring LR11 on a cell surface in a sample to be tested.

22 Claims, 7 Drawing Sheets

(56) References Cited

OTHER PUBLICATIONS

Jiang, M., et al., "Ang II-stimulated migration of vascular smooth muscle cells is dependent on LR11 in mice," The Journal of Clinical Investigation, vol. 118, No. 8, pp. 2733-2746, (Aug. 2008).

Matsuo, M., et al., "Development of an Immunoassay for the Quantification of Soluble LR11, a Circulating Marker of Atherosclerosis," Clinical Chemistry, vol. 55, No. 10, pp. 1801-1808, (2009).

Zhang, X., et al., "Identification of four human cDNAs that are differentially expressed by early hematopoietic progenitors," Experimental Hematology, vol. 28, pp. 1286-1296, (2000).

International Search Report dated Sep. 27, 2011 in PCT/JP11/66276 Filed Jul. 15, 2011.

Office Action dated Mar. 14, 2016, in European Patent Application No. 11806924.4.

Ledesma et al, "Low-Density Lipoprotein Receptor (LDLR) Family: The Uptake of Cholesterol", emerging Drugs and Targets for Alzheimer's Disease, May 7, 2010, pp. 43-44, Cambridge ISBN: 978-1-84973-963-1.

Office Action dated Jun. 20, 2016 in European Patent Application No. 11 806 924.4.

Dov Greenbaum, et al., "Interrelating Different Types of Genomic Data, from Proteome to Secretome: 'Oming in on Function", Genome Research, XP9088703A, vol. 11, No. 9, Sep. 11, 2001, pp. 1463-1468.

J.W. Vardiman,"The World Health Organization (WHO) classification of tumors of the hematopoietic and lymphoid tissues: An overview with emphasis on the myeloid neoplasms", Chemico-Biological Interactions 184(2010) 16-20.

Examiner's email dated May 12, 2017 regarding amendment for European Patent Application No. 11806924.4.

* cited by examiner

METHOD FOR DETECTING MALIGNANT TUMOR CELLS

FIELD OF THE INVENTION

The present invention relates to a method for detecting a malignant tumor cell.

BACKGROUND OF THE INVENTION

A protein specifically expressed on a tumor cell surface is useful as a cell surface marker for cancer diagnosis using peripheral blood, bone marrow cells, tissues, and the like of a patient, and is also applicable to evaluation of an effect of cancer treatment and monitoring of recurrence by examining the presence or absence of expression of the protein.

In addition, in recent years, an antibody drug which targets a protein specifically expressed on a tumor cell surface has been actively developed. A therapeutic method using an antibody drug has attracted attention as a therapeutic method which has a minimal influence on normal cells and can be expected to provide a therapeutic effect having high selectivity for tumor cells by selecting as a target an antigen which is not expressed or is expressed in a very small amount in normal cells. An antibody as an active ingredient of the antibody drug has a variety of modes (mechanisms) of action. For example, a therapeutic drug for B cell lymphoma, rituximab, which uses a monoclonal antibody produced against a CD20 antigen specifically expressed in B cells, has actions such as induction of apoptosis, an antibody-dependent cellular cytotoxicity (ADCC) activity, and a complement-dependent cytotoxicity (CDC) activity on tumor cells. Further, yttrium ($^{90}$Y) ibritumomab tiuxetan, in which a radioisotope is bound to an anti-CD20 monoclonal antibody, is expected to provide a therapeutic effect by radiation as well as attack on tumor cells by the antibody, and has been found to be useful for treatment of recurrent or refractory B-cell lymphoma.

Under current circumstances, however, applications of a monoclonal antibody useful for tumor treatment are limited to several kinds of tumors such as metastatic breast cancer, acute myeloid leukemia, refractory chronic lymphoma, non-Hodgkin's lymphoma, and multiple myeloma.

Accordingly, a novel cell surface marker specific for tumor cells, which is applicable to cancer diagnosis and cancer treatment using an antibody drug, has been actively searched.

LDL receptor relative with 11 ligand-binding repeats (LR11) was a novel LDL receptor-like protein identified as having a characteristic structure to the LDL receptor family (Patent Document 1 and Non Patent Document 1). Expression of LR11 is reported to be promoted specifically invascular intima thickened sites formed by migration and proliferation of smooth muscle cells (Non Patent Document 2). The inventors found that: soluble LR11 was present in blood of mammals and concentrations of soluble LR11 in blood of arteriosclerosis disease patients showed significantly higher values than those of healthy subjects (Patent Document 2). In addition, the inventors developed a method to measure soluble LR11 in blood or bone marrow aspirates simply and exactly (Patent Document 3 and Non Patent Document 4), and measured concentrations of soluble LR11 in various diseases. As a result, the inventors confirmed that the concentrations of soluble LR11 showed abnormally high values in malignant tumors, in particular, hematopoietic tumor diseases such as leukemia and malignant lymphoma, and found that soluble LR11 in blood served as a novel tumor marker (Patent Document 4). However, the concentrations of soluble LR11 do not always show abnormally high values in blood of all hematopoietic tumor disease patients, and a reason for that has not been clarified yet.

Meanwhile, Non Patent Document 5 reports that LR11 mRNA is expressed in a wide range of human-derived tissues (nerve tissues, liver, brain, and peripheral leukocytes). In addition, the document describes that the expression of LR11 mRNA is promoted in a CD34+CD38-fraction (myeloid leukemia cells) in which stem cells in human bone marrow cells are present, and although data is not shown, LR11 mRNA is expressed in part of hematopoietic tumor culture cells as well. However, Non Patent Document 5 merely describes exhaustive gene expression analysis in blood precursor cells including culture cells, does not describe any tissue expressing LR11 at a protein level, and also does not describe any relationship between a hematopoietic tumor and expression of LR11 mRNA at all.

PRIOR ART

Patent Document

Patent Document 1: JP-A-09-163988
Patent Document 2: WO 2008/155891 A1
Patent Document 3: WO 2009/116268 A1
Patent Document 4: JP 2009-285492

Non Patent Document

Non-Patent Document 1: J. Biol. Chem. 1996; 271, 24761-24768
Non-Patent Document 2: Arterioscler. Thromb. Vasc. Biol. 1999; 19, 2687-2695
Non-Patent Document 3: J. Clin. Invest. 2008; 118, 2733-2746
Non-Patent Document 4: Clin. Chem. 2009; 55, 1801-1808
Non-Patent Document 5: Experimental Hematology 2000; 28, 1286-1296

SUMMARY OF THE INVENTION

Problem to be Solved by the Invention

An object of the present invention is to provide a method for detecting a malignant tumor cell by measuring a protein marker expressed on a malignant tumor cell surface.

Another object of the present invention is to provide a therapeutic drug for a malignant tumor, including as an active ingredient an antibody specific for a surface protein of a malignant tumor cell.

Means for Solving the Problem

The inventors of the present invention have produced an anti-LR11 antibody, and have made studies on the reactivity of the antibody. As a result, the inventors have found that each of LR11 in a lysate of a hematopoietic tumor cell line and LR11 secreted into a culture supernatant of the hematopoietic tumor cell line can be detected. Further, the inventors have found that when a bone marrow tissue is subjected to immunostaining, LR11 is positive in such a hematopoietic tumor patient that the concentration of soluble LR11 in serum shows a high value, and LR11 is positive in such a hematopoietic tumor patient that the concentration of soluble LR11 in serum shows a value within a normal range (based on Non Patent Document 4 and the like) as well in some cases.

In addition, the inventors have performed flow cytometry through the use of the produced anti-LR11 antibody. As a result, the inventors have confirmed for the first time that LR11 is expressed on surfaces of many hematopoietic tumor-derived cell lines. Further, the inventors have confirmed that LR11 is expressed in an immature monocyte fraction in peripheral blood of an acute myeloid leukemia patient, and LR11 is not expressed in mature B cells in peripheral blood of an acute lymphoblastic leukemia patient, whereas LR11 is expressed in an immature B cell fraction during a differentiation process. Meanwhile, the inventors have confirmed that LR11 is expressed on a cell surface in a carcinoma-derived cell line as well. Based on such findings, the inventors have found that the presence of a malignant tumor cell can be specifically detected by measuring LR11 on a cell surface in a sample to be tested even when the concentration of soluble LR11 in blood does not show a significantly high value, and that LR11 can serve as a target molecule for an antibody drug because it is expressed on a malignant tumor cell surface. Thus, the present invention has been completed.

That is, the present invention provides a method for detecting a cell of a malignant tumor, including measuring LR11 on a cell surface in a sample to be tested.

The present invention also provides a method for diagnosing a malignant tumor, including measuring LR11 on a cell surface in a sample to be tested.

The present invention also provides a therapeutic drug for a malignant tumor, including as an active ingredient an antibody specific for LR11 on a malignant tumor cell surface.

The present invention also provides an antibody specific for LR11 on a malignant tumor cell surface, for treatment of a malignant tumor.

The present invention also provides a use of an antibody specific for LR11 on a malignant tumor cell surface, for manufacture of a therapeutic drug for a malignant tumor.

The present invention also provides a therapeutic method for a malignant tumor, including administering an antibody specific for LR11 on a malignant tumor cell surface.

Effects of Invention

According to the present invention, it is possible to detect a malignant tumor, in particular, a hematopoietic tumor or a carcinoma with high accuracy by a less invasive technique, and to obtain useful information in determining the presence of a malignant tumor and the severity thereof, selecting a therapeutic method therefor and evaluating the effect of the therapeutic method, and estimating the risk of recurrence of the malignant tumor and determining the presence or absence of the recurrence. It is also possible to treat a malignant tumor by specifically attacking a malignant tumor cell.

EMBODIMENTS FOR CARRYING OUT THE INVENTION

Figure 1:
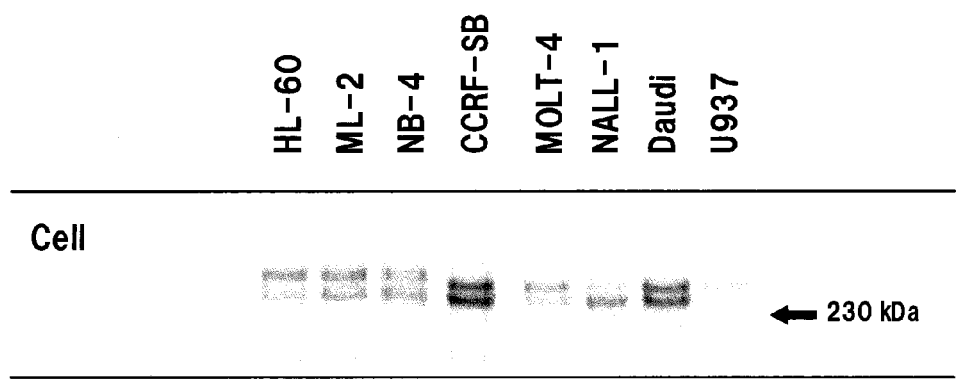
FIG. 1 An image showing the expression of LR11 in various hematopoietic tumor cell lines detected by a western blot method through the use of their cell lysates.

As used herein, unless otherwise stated, "LR11" refers to a protein having reactivity with an anti-LR11 antibody, and refers to a protein known as "full-length LR11" or "soluble LR11" or a partially fragmented or modified product thereof. Further, as used herein, the terms "measurement" and "detection" have the same meaning. Unless otherwise stated, the terms encompass all the concepts of "qualitative" measurement, "quantitative" measurement, and "semi-quantitative" measurement. Further, "quantitative" and "semi-quantitative" are sometimes collectively referred to as "quantitative and the like."

As used herein, the diagnosis of a malignant tumor encompasses determining the presence of a malignant tumor or the severity thereof, selecting a therapeutic method therefor or evaluating the effect of the therapeutic method, and estimating the risk of recurrence of the malignant tumor or determining the presence or absence of the recurrence.

A detection method for a malignant tumor cell of the present invention includes measuring LR11 on a cell surface in a sample to be tested. The sample to be tested has only to be a living body-derived sample suspected of the presence of a malignant tumor cell, and examples thereof include peripheral blood, bone marrow aspirates, and tissue sections. Further, the sample to be tested may be derived from mammals such as mice, rats, rabbits, pigs, dogs, and cats as well as humans, for example.

A malignant tumor to be detected in the present invention includes a hematopoietic tumor and a carcinoma. In this case, the hematopoietic tumor includes leukemia and malignant lymphoma. Leukemia includes acute leukemia and chronic leukemia, and malignant lymphoma includes non-Hodgkin's lymphoma. On the other hand, examples of the carcinoma include stomach cancer, liver cancer, pancreatic cancer, lung cancer, prostate cancer, bladder cancer, esophageal cancer, breast cancer, cervical cancer, ovarian cancer, colon cancer, large bowel cancer, kidney cancer, gallbladder cancer, neurotumor (glioma), and malignant melanoma. As a specific target to be detected in the present invention, in the hematopoietic tumor, acute leukemia is more preferred out of leukemia, and non-Hodgkin's lymphoma is more preferred out of malignant lymphoma. Further, in the carcinoma, liver cancer, pancreatic cancer, colon cancer, large bowel cancer, and gallbladder cancer are preferred.

A method for measuring LR11 on a cell surface includes a method using a protein which specifically binds to LR11 on a cell surface, such as an anti-LR11 antibody or an LR11 receptor-associated protein (RAP). In particular, means for measuring LR11 on a cell surface through the use of an anti-LR11 antibody is preferred in terms of accuracy and specificity.

The anti-LR11 antibody which reacts with LR11 on a cell surface may be a monoclonal antibody or a polyclonal antibody. Of those, a monoclonal antibody is preferably employed. The antibody may be produced by a well-known method. For example, in the production of the polyclonal antibody, animals such as mice, rats, hamsters, rabbits, goats, sheep, and chickens are used to be immunized by the immunogen. The polyclonal antibody is preferably anti-serum. Anti-serum may be prepared by, for example, subcutaneously, intradermally, or intraperitoneally administering an antigen to an animal once or multiple times, and recovering anti-serum from serum of the immunized animal. When a protein or a peptide is used as an antigen, immunization is more preferably performed through the use of a mixture of an immunogen and an adjuvant exhibiting an immunostimulating effect.

Further, the monoclonal antibody may be produced by a known method of producing a monoclonal antibody, e.g., "Monoclonal Antibody" (Hideaki NAGAMUNE and Hiroshi TERADA, Hirokawa-shoten, 1990) or "Monoclonal Antibody" (Jame W. Golding, 3rd edition, Academic Press, 1996). Alternatively, the monoclonal antibody may be produced through DNA immunization with reference to Nature 1992 Mar. 12; 356 152-154 or J. Immunol. Methods March 1; 249 147-154.

The antigen employed in the production of the antibody may be LR11, a fragment thereof (peptide), a cell expressing LR11 on the cell surface, or an expression vector including cDNA encoding LR11. In order to produce a monoclonal antibody which recognizes the high-order structure of LR11, an expression vector having inserted therein a full-length human LR11 gene is the most suitable. Alternatively, an expression vector having inserted therein a part of LR11 sequence may be used. The DNA immunization may be performed by subcutaneously injecting one or more of the expression vectors separately or in combination to animals (e.g., mice or rats) to be immunized via any one of various gene transfection methods (e.g., intramuscular injection, electroporation, and gene gun-mediated immunization) for incorporation of the expression vector(s) into cells.

The monoclonal antibody may be produced through a method including culturing hybridomas produced by a conventional method and isolating a target antibody from the culture supernatant, or a method including administering the hybridomas to a mammal compatible with the hybridomas and collecting ascites of the mammal.

If required, the anti-LR11 antibody may be purified before use from anti-serum, a culture supernatant, or ascites. Examples of the anti-LR11 antibody purification/isolation method include conventionally known methods such as salting out (e.g., ammonium sulfate precipitation), gel filtration (e.g., by use of Sephadex), ion-exchange chromatography, and affinity purification (e.g., by use of protein A column).

A specific measurement method for LR11 on a cell surface in a sample to be tested using an anti-LR11 antibody is not particularly limited, and examples thereof include flow cytometry, an immunohistostaining method, and a western blot method for a cell membrane fraction. Of those, flow cytometry is preferred. In the case of employing flow cytometry, an anti-LR11 antibody labeled with a fluorescent dye is subjected to a reaction with a cell population in a sample, washed with physiological saline or any other medium, and then subjected to fluorescence staining pattern analysis and cell sorting through the use of a fluorescence-activated cell sorter (FACS) commercially available from Becton, Dickinson and Company and others. It should be noted that a substance having affinity with LR11, such as RAP, may be used as an alternative to the anti-LR11 antibody as long as the substance binds to LR11 on a cell surface, and such embodiment mode falls within the scope of the present invention.

In the measurement of LR11 of the present invention, in addition to qualitative measurement, which measures the presence or absence of expression of LR11 on a cell surface, quantitative measurement or semi-quantitative measurement may be performed by comparison with the concentration or amount of LR11 to serve as a calibration standard. In this case, the concentration or amount of LR11 to serve as a calibration standard may be set through the use of, for example, an LR11 expressing cell or LR11 expressing cell line lysate having a known concentration or amount, LR11 collected from a culture supernatant or blood containing LR11 at a high concentration, recombinant LR11, or a synthetic peptide which may be used as an immunogen in antibody production.

In the method of the present invention, for example, detailed information about a pathological condition may be obtained by comparing the measurement results (qualitative and quantitative and the like) of LR11 in a sample to be tested, with the measurement results (qualitative and quantitative and the like) of a healthy subject group or a particular cancer patient group classified based on the kind of a tumor and the like, measured in advance. For example, when a malignant tumor cell is present, when the severity is higher, or when there is a risk of recurrence, the concentration or amount of LR11 on a cell surface in a sample to be tested may show a higher value than a measured value for a healthy subject group or a particular cancer patient group. The comparison of both the values enables determination of the presence of a malignant tumor or the severity thereof, selection of a therapeutic method therefor or evaluation of the effect of the therapeutic method, or estimation of the risk or recurrence of the malignant tumor or determination of the presence or absence of the recurrence.

Specific examples of the measurement method and the determination method include the following means. In the measurement by flow cytometry, positive and negative cut-offs are set, and the determination may be performed based on the abundance ratio of positive cells in a certain cell population. Further, in the measurement by immunohisto-staining, positive and negative cutoffs are set, and the determination may be performed based the ratio (width) of a positive region in a certain tissue range, and by image analysis on the localization state of the positive region, the state of the boundary with a normal region, and the like. Further, in the determination, the accuracy of the determination may be improved by employing a conventionally known method such as combination with a cell surface marker other than LR11 to be described later.

The severity of a malignant tumor is an index for the degree of progress of cancer. In the present invention, in the case of, for example, a hematopoietic tumor, the expression "determination of the presence of a malignant tumor or the severity thereof" may refer to classification of the tumor according to the WHO classification based on a result of measurement of LR11 on a tumor cell surface, because leukemia and malignant lymphoma are classified therein in detail and the severity thereof is also evaluated therein. Further, non-Hodgkin's lymphoma is classified by WHO into "high grade malignancy," "intermediate grade malignancy," and "low grade malignancy" in terms of cell proliferation rate. In this case, the above-mentioned expression may refer to this classification procedure based on a result of measurement of LR11 on a tumor cell surface. Typical examples of the non-Hodgkin's lymphoma classified into each grade of malignancy include follicular lymphoma (low grade malignancy), diffuse large B-cell lymphoma (intermediate to high grade malignancy), and T-lymphoblastic lymphoma (high grade malignancy). Further, carcinoma is classified according to the TNM classification, which is an internationally accepted stage classification and based on the tumor dimensions and degree of progress, status of metastasis to regional lymph nodes, and the presence or absence of distant metastasis. There is also employed a further stage classification based on this classification, which can provide both the degree of cancer progression and the degree of spreading of cancer. In the case of carcinoma, the above-mentioned expression may refer to these classification procedures based on a result of measurement of LR11 on a tumor cell surface.

Selection of a therapeutic method and evaluation of the effect of the therapeutic method can be assessed by monitoring the change of the ratio of leukemia blast cells to whole bone marrow cells and the dimensional changes of the onset tumor. Further, when indexes for cell surface LR11 (e.g., concentration, amount, the abundance ratio of positive cells, and the ratio of a positive region in the tissue) are not lowered to normal levels after treatment, the risk of recurrence can be estimated to be high. As for the presence or absence of recurrence, when the indexes for cell surface LR11 rise or increase during an interval stage or after remission achieved by treatment, the possibility of recurrence of a tumor can be evaluated to be high.

At present, in the diagnosis of leukemia, bone marrow aspiration and normal staining are performed for definite diagnosis when an abnormality is found in a blood morphology test using peripheral blood, and for more detailed classification, a cell surface antigen analysis test is performed. According to the measurement method for LR11 on a cell surface in a sample to be tested using an anti-LR11 antibody of the present invention, the accuracy of detection of a leukemia cell can be improved in a test using peripheral blood. Further, in determining the presence of the malignant tumor cell and the like, the determination can be performed with higher accuracy by using a measured value for LR11 on a cell surface in combination with any other known cell surface marker.

In blood cells, when hematopoietic stem cells differentiate into various series of cells, the kind and timing of expression of an epitope to be expressed vary depending on the degree of cell differentiation and maturation. Various molecules such as an antigen receptor, a cell adhesion molecule, a cytokine receptor, a complement receptor, and an Fc receptor are present on the surface of hematopoietic cells. Each of those molecules can be used as a marker to estimate types of cells. Further, in the disease type diagnosis of leukemia, a cytochemical technique is employed, and the classification of lymphoblastic leukemia and myeloid leukemia is performed by utilizing a peroxidase reaction (POD). M0 in FAB classification as one of the acute leukemia classifications is 3% or less in terms of POD, and has been conventionally classified into lymphatic leukemia. At present, however, as a result of search of cell surface antigens, in the case where a marker CD13 or CD33 is positive and CD19 and CD20 are negative, treatment of myeloid leukemia is started. Like M0, M7 is 3% or less in terms of POD, and thus the search of surface antigens is important. Lymphoblastic leukemia and malignant lymphoma do not have very clear morphological features unlike myeloid leukemia, and hence the search of cell surface antigens is a more important test item. As described above, the search of cell surface traits plays an important role in the decision of types of tumor cells, and the WHO classification describes immunophenotypes of all hematopoietic tumors. The combination of each of those conventional methods with LR11 of the present invention as a cell surface marker can provide information for grasping a pathological condition in more detail. It should be noted that the diagnosis, classification, and the like of leukemia described above have been described in detail in, for example, Shigetaka Asano et al. (Ed.), "Miwa's Hematology," BUNKODO CO., LTD. (2006), which may be used for reference in carrying out the measurement of the present invention.

The present invention has confirmed that LR11 is expressed on a malignant tumor cell surface. Thus, molecular target treatment using LR11 on a malignant tumor cell surface as a target molecule, specifically, treatment of a malignant tumor using an antibody specific for LR11 is possible. The molecular target treatment may be performed by administering a therapeutic drug for a malignant tumor containing an anti-LR11 antibody as an active ingredient, a so-called antibody drug. It should be noted that as used herein, the "therapeutic drug for a malignant tumor" and the "antibody drug" are used synonymously without being particularly distinguished from each other.

In the antibody drug, the anti-LR11 antibody may be used as a carrier for carrying a radioisotope, an anti-cancer agent, a toxin, or the like (hereinafter, sometimes collectively referred to as "anti-cancer agent or the like"). In this case, the anti-LR11 antibody serves as a carrier for transporting an anti-cancer agent or the like to malignant tumor cells (target cells) expressing a target molecule (LR11). As the anti-cancer agent or the like to be carried by the anti-LR11 antibody, a radioisotope is preferably used, and $^{90}Y$ (yttrium 90) or $^{131}I$ (iodine 131) is suitably used.

The antibody drug can directly exert a cytocidal effect when the anti-LR11 antibody contained in the drug has a cytotoxicity activity. According to recent findings, the cytotoxicity activity is considered to be important in the mechanisms of action of the antibody drug. Thus, an antibody which binds to LR11 expressed on a malignant tumor cell surface and has a cytotoxicity activity is preferred. Such an antibody is obtained by screening the anti-LR11 antibody produced as described above for the presence of the cytotoxicity. It should be noted that in the present invention, the "cytotoxicity" refers to providing a pathological change on cells in some way, and refers to not only directly killing and damaging cells based on an ADCC activity and a CDC activity, but also structural and functional damages on all cells, such as cleavage of DNA, formation of a base dimer, chromosomal breakage, damage on a mitotic apparatus, and reductions in activities of various enzymes. In the present invention, the "cytotoxicity activity" refers to the property of causing the cytotoxicity. Further, a malignant tumor as a target of the therapeutic drug for a malignant tumor of the present invention is the same as the detection target described above.

The anti-LR11 antibody to be used in the therapeutic drug (antibody drug) for a malignant tumor of the present invention is not particularly limited as long as the antibody specifically binds to LR11. Specific examples thereof may include an antibody derived from an immune animal such as a mouse, an antibody derived from the same animal as a mammal as a therapeutic target, a chimeric antibody, a humanized antibody, and a complete human antibody. Those antibodies may be appropriately selected from those as described above in consideration of a dosage for a mammal as an administration target, an administration frequency, antigenicity, and the like. When the administration target of the antibody drug is a human, a chimeric antibody, a humanized antibody, or a complete human antibody is preferably used. The chimerization, humanization, or the like may be performed by a known method.

The ADCC activity or the CDC activity may be imparted to the anti-LR11 antibody or enhanced by employing a known method. A method for imparting the ADCC activity and/or the CDC activity to the anti-LR11 antibody or enhancing these activities includes methods such as modifying an amino acid sequence in an Fc region of an antibody (Shields R. L., et. al.; J. Biol. Chem., 276, 6591-6604 (2001)), modifying a sugar chain in an Fc region to increase a binding ability to an Fcγ receptor IIIA (Umana P., et. al; Nat. Biotechnol., 17, 176-180 (1999), Shields R. L., et. al; J. Biol. Chem., 277 26733-26740 (2002), Shinkawa T., et. al.; J. Biol. Chem., 278, 3466-3473 (2003)), polymerizing an Fc region tandemly (WO 2007/100083 A1), and introducing an Fc fragment having an ability to enhance a CDC activity (WO 2006/114700 A1).

Furthermore, an antibody which neutralizes or inhibits the bioactivity of LR11 in tumor cells, selected from the anti-LR11 antibodies, may be used as an antibody drug whose mechanism of action is induction of apoptosis in malignant tumor cells.

The in vitro neutralization activity of the anti-LR11 antibody on the bioactivity of LR11 in tumor cells may be evaluated, for example, by adding the anti-LR11 antibody at various concentrations to a culture system of cells overexpressing LR11 and measuring the degree of suppression of adhesion and migration activities possessed by LR11. Alternatively, the activity may be evaluated by measuring a change in sensitivity of tumor cells to an anti-cancer agent. Further, in the case of using carcinoma cells overexpressing LR11, the activity may be evaluated by measuring activities to suppress focus formation, colony formation, and spheroid growth.

An in vitro cytotoxicity activity of an anti-LR11 antibody on tumor cells may be evaluated, for example, by measuring an antibody-dependent cellular cytotoxicity activity, a complement-dependent cytotoxicity activity, or a complement-dependent cellular cytotoxicity activity to be exhibited by the anti-LR11 antibody in cells overexpressing LR11. For example, the activity may be evaluated by culturing cells overexpressing LR11, adding an anti-LR11 antibody at various concentrations to the culture system, further adding spleen cells of mice or the like, culturing the cells for an appropriate time, and then measuring a rate of induction of cell death for the cells overexpressing LR11.

An in vitro therapeutic effect of an anti-LR11 antibody on a tumor utilizing an experimental animal may be evaluated, for example, by administering the anti-LR11 antibody to a transgenic model animal overexpressing LR11 out of leukemia model animals such as WT1 gene transgenic mice, and measuring a change of tumor cells. The thus obtained antibody which neutralizes the bioactivity of LR11 or antibody which specifically damages tumor cells expressing LR11 is useful as a drug, in particular, as an active ingredient for an antibody drug for the purpose of cancer treatment.

The present invention also provides a pharmaceutical composition containing a therapeutically effective amount of the anti-LR11 antibody, and a pharmaceutically acceptable diluent, carrier, solubilizer, emulsifier, preservative, and/or aid.

A substance to be used for formulation acceptable in the pharmaceutical composition of the present invention is preferably non-toxic for a person to which the pharmaceutical composition is administered in terms of preferably a dosage and an administration concentration.

The pharmaceutical composition of the present invention may contain a substance for formulation for changing, maintaining, or retaining a pH, an osmotic pressure, viscosity, a degree of transparency, color, isotonicity, sterility, stability, a rate of dissolution, a rate of sustained release, a rate of absorption, and a rate of permeation. Examples of the substance for formulation may include, but not limited to: an amino acid such as glycine, alanine, glutamine, asparagine, arginine, or lysine; an antimicrobial agent; an antioxidant such as ascorbic acid, sodium sulfate, or sodium bisulfite; a buffer such as a phosphate, citrate, or borate buffer, or a hydrogencarbonate or Tris-hydrochloric acid (Tris-HCl) solution; a filler such as mannitol; a chelating agent such as ethylenediaminetetraacetic acid (EDTA); a complexing agent such as caffeine, polyvinylpyrrolidine, β-cyclodextrin, or hydroxypropyl-β-cyclodextrin; an expander such as glucose, mannose, or dextrin; a monosaccharide, a disaccharide, or any other carbohydrate such as glucose, mannose, or dextrin; a colorant; a flavoring agent; a diluent; an emulsifier; a hydrophilic polymer such as polyvinylpyrrolidine; a low-molecular-weight polypeptide; a salt forming counter ion; a preservative such as benzalkonium chloride, benzoic acid, salicylic acid, thimerosal, phenethyl alcohol, methylparaben, propylparaben, chlorhexidine, sorbic acid, or hydrogen peroxide; a solvent such as glycerin, propylene glycol, or polyethylene glycol; a sugar alcohol such as mannitol or sorbitol; a suspending agent; PEG; sorbitan ester; a polysorbate such as polysorbate 20 or polysorbate 80; a surfactant such as Triton, tromethamine, lecithin, or cholesterol; a stabilization enhancing agent such as sucrose or sorbitol; an elasticity enhancing agent such as sodium chloride, potassium chloride, mannitol, or sorbitol; a transporting agent; a diluent; an excipient; and/or a pharmaceutical aid. The addition amount of each of those substances for formulation is preferably 0.01 to 100-fold, more preferably 0.1 to 10-fold, with respect to the weight of the anti-LR11 antibody. A suitable composition of the pharmaceutical composition in a formulation may be appropriately determined by a person skilled in the art depending on an applied disease, an applied administration route, and the like.

The excipient or the carrier in the pharmaceutical composition may be a liquid or a solid. An appropriate excipient or carrier may be water for injection, physiological saline, artificial cerebrospinal fluid, or any other substance to be generally used in parenteral administration. Neutral physiological saline or physiological saline containing serum albumin may also be used for the carrier. The pharmaceutical composition may contain a Tris buffer having a pH of 7.0 to 8.5 and an acetate buffer having a pH of 4.0 to 5.5, and may contain sorbitol or any other compound in addition to the buffers. The pharmaceutical composition of the present invention is prepared as a lyophilized product or a liquid, as an appropriate medicament having a selected composition and a required purity. The pharmaceutical composition containing the anti-LR11 antibody may be formed as a lyophilized product using an appropriate excipient such as sucrose.

The pharmaceutical composition of the present invention may be prepared for parenteral administration, or may be prepared for gastrointestinal absorption through oral administration. The composition and concentration of the formulation may be determined according to an administration method. With regard to affinity with LR11, i.e., a dissociation constant (Kd value) for LR11, of the anti-LR11 antibody, which is contained in the pharmaceutical composition of the present invention; the higher the affinity becomes (or the lower Kd value is), the lower the dosage level to humans can be made to exhibit drug efficacy. Hence, the dosage of the pharmaceutical composition of the present invention to humans may also be determined based on the affinity of the anti-LR11 antibody for LR11. For the dosage in the case of administering a human type anti-LR11 antibody to humans, the antibody has only to be administered at about 0.1 to 100 mg/kg once per 1 to 30 days.

The form of the pharmaceutical composition of the present invention is exemplified by an injectable preparation including drops, a suppository, a transnasal preparation, a sublingual preparation, and a transdermal absorption preparation. Of these, an injectable preparation including drops is preferred.

EXAMPLES

The present invention is described in details as follows.

Example 1: Confirmation of Expression of LR11 in Various Hematopoietic Tumor Cell Lines The expression of LR11 in various hematopoietic tumor cell lines was confirmed by a western blot method using an anti-LR11 monoclonal antibody (A2-2-3: Patent Document 3) produced through immunization with a synthetic peptide having a partial amino acid sequence of LR11. The following cell lines were used: a total of eight kinds of cell lines including three lines derived from acute myeloid leukemia (HL-60, ML-2, and NB-4), three lines derived from acute lymphoblastic leukemia (CCRF-SB, MOLT-4, and NALL-1), and two lines derived from malignant lymphoma (Daudi and U937). Those cell lines were each suspended in an HT medium (RPMI-1640 containing 15% fetal bovine serum, HT supplement, andpenicillin/streptomycin), and cultured and proliferated in a 5% $CO_2$ incubator at 37° C. for an appropriate time. The number of cells was counted for each of the cell lines, and the cells were fractionated so that the number of the cells was $1 \times 10^7$, and then dissolved by addition of an RIPA buffer (25 mM Tris-HCl pH 7.6, 150 mM NaCl, 1% NP-40, 1% sodium deoxycholate, and 0.1% SDS) containing a 1% protease inhibitor (manufactured by Sigma-Aldrich; P8340). Insoluble matter was removed by centrifugation. After that, the cell lysates were measured for their concentrations of proteins, and 20 μg per lane thereof were subjected to boiling treatment under a reductive condition containing SDS. The treated liquids were applied to the respective lanes of SDS-PAGE (2 to 15%) and subjected to electrophoresis. After the electrophoresis, the proteins were transferred from the gel to a PVDF membrane and subjected to a reaction with the anti-LR11 monoclonal antibody (A2-2-3) as a primary antibody. Then, LR11 was detected through the use of a mouse IgG ABC kit (manufactured by Vector).

As a result, two bands slightly different in size were observed at positions corresponding to molecular weights of slightly more than 230 kDa in the cell lysate of each of the cell lines (FIG. 1).

Example 2: Flow Cytometry of Various Hematopoietic Tumor Cell Lines

Figure 2:
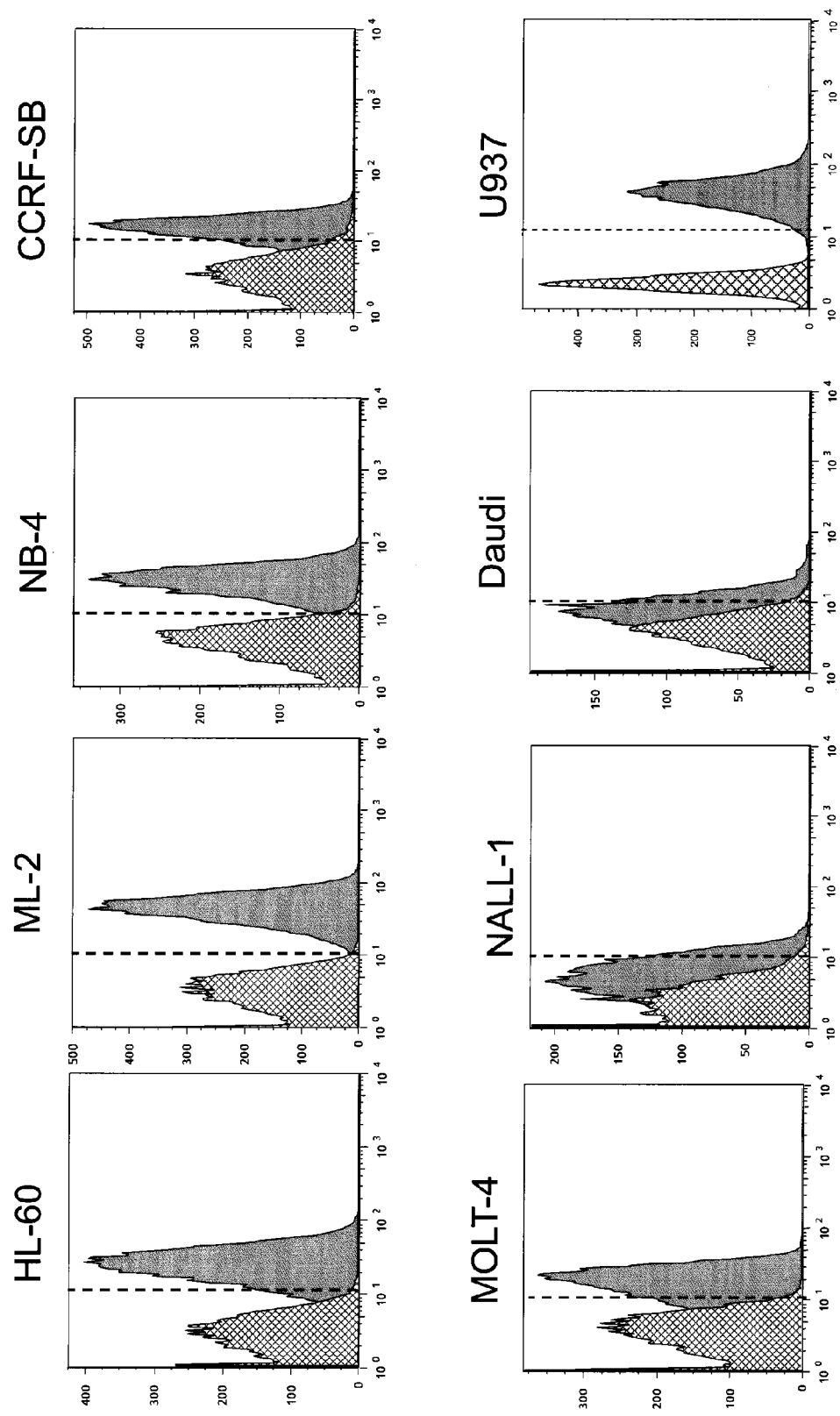
FIG. 2 Graphs showing the results of analysis on the expression of LR11 on a cell surface in various hematopoietic tumor cell lines by flow cytometry.

The presence or absence of expression of LR11 on a cell surface in the eight kinds of cell lines, which had been analyzed in Example 1, was analyzed by flow cytometry. $5 \times 10^5$ cells of each of the cell lines were floated in a Staining Medium (1% FBS/PBS) and centrifuged at 1,500 rpm for 5 minutes, and then the supernatant was removed. To the pellet were added 3 μl, of a 1 mg/mL FITC-labeled anti-LR11 monoclonal antibody (M3: Patent Document 3), and the mixture was subjected to a reaction at 4° C. for 60 minutes. The cells were washed twice with the Staining Medium, and then flow cytometry analysis was carried out through the use of JSAN (manufactured by Bay bioscience) according to the instruction manual. Normal mouse IgG (manufactured by BD pharmingen) was used as a negative control for the FITC-labeled anti-LR11 monoclonal antibody. FIG. 2 shows the results. Six cell lines, i.e., HL-60, ML-2, NB-4, MOLT-4, CCRF-SB, and U937, out of the eight cell lines whose expression of LR11 had been confirmed in Example 1, showed strongly positive to weakly positive reactions. Hence, LR11 was found to be expressed on surfaces of those cell lines.

Figure 3:
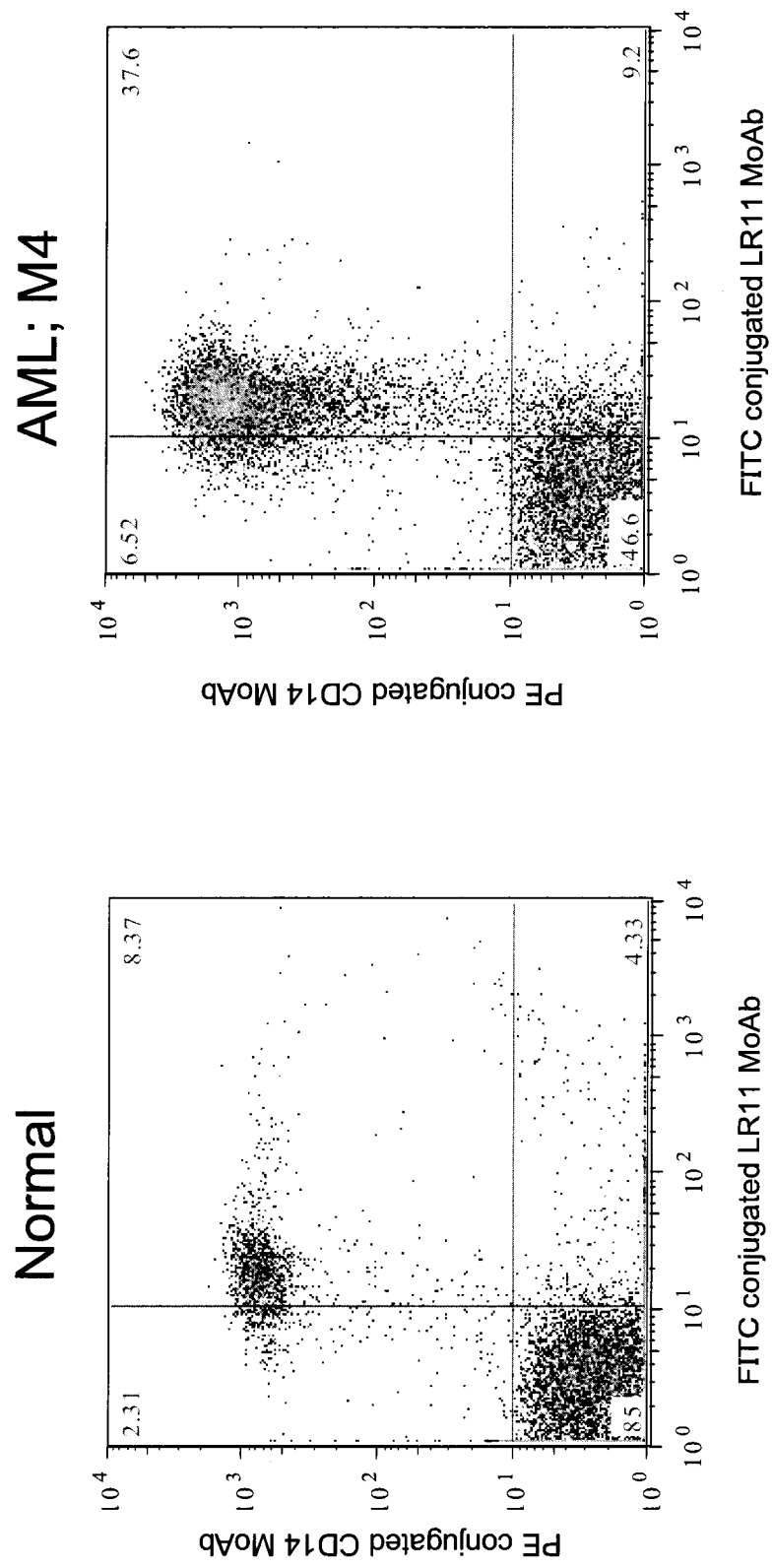
FIG. 3 Graphs showing the results of analysis on the expression of CD14 and LR11 on a cell surface in peripheral blood of a healthy subject and an acute myelomonocytic leukemia patient by flow cytometry.

Example 3: Flow Cytometry of Peripheral Blood of Acute Myeloid Leukemia (AML) Patient Mononuclear leukocytes were separated from peripheral blood of an acute myelomonocytic leukemia patient (FAB classification: M4) through the use of Ficoll-Paque PLUS (manufactured by GE Healthcare), and the presence or absence of expression of LR11 on a cell surface was analyzed by flow cytometry as described in Example 2. Peripheral blood of a healthy subject was used as a negative control. $5 \times 10^5$ cells of each of the cell lines were floated in a Staining Medium and centrifuged at 1,500 rpm for 5 minutes, and then the supernatant was removed. To the pellet were added 3 μL each of a 1 mg/mL FITC-labeled anti-LR11 monoclonal antibody (M3) and a PE-labeled anti-CD14 antibody (manufactured by BD pharmingen), and the mixture was reacted at 4° C. for 60 minutes. The cells were washed twice with the Staining Medium, and then flow cytometry analysis was carried out through the use of JSAN (manufactured by Bay bioscience) according to the instruction manual. FIG. 3 shows the results.

In leukocytes in the peripheral blood of the healthy subject, LR11 was found to be expressed in a positive fraction of CD14 as a monocyte surface marker. Similarly, also in leukemia cells in the peripheral blood of the acute myelomonocytic leukemia patient, LR11 was found to be expressed in CD14-positive monocytic blasts. Many immature monocytes such as monoblasts and promonocytes are observed in leukemia. Thus, LR11 was found to be expressed in immature monocytes as leukemia cells, as well as mature monocytes observed in a healthy subject.

Figure 4:
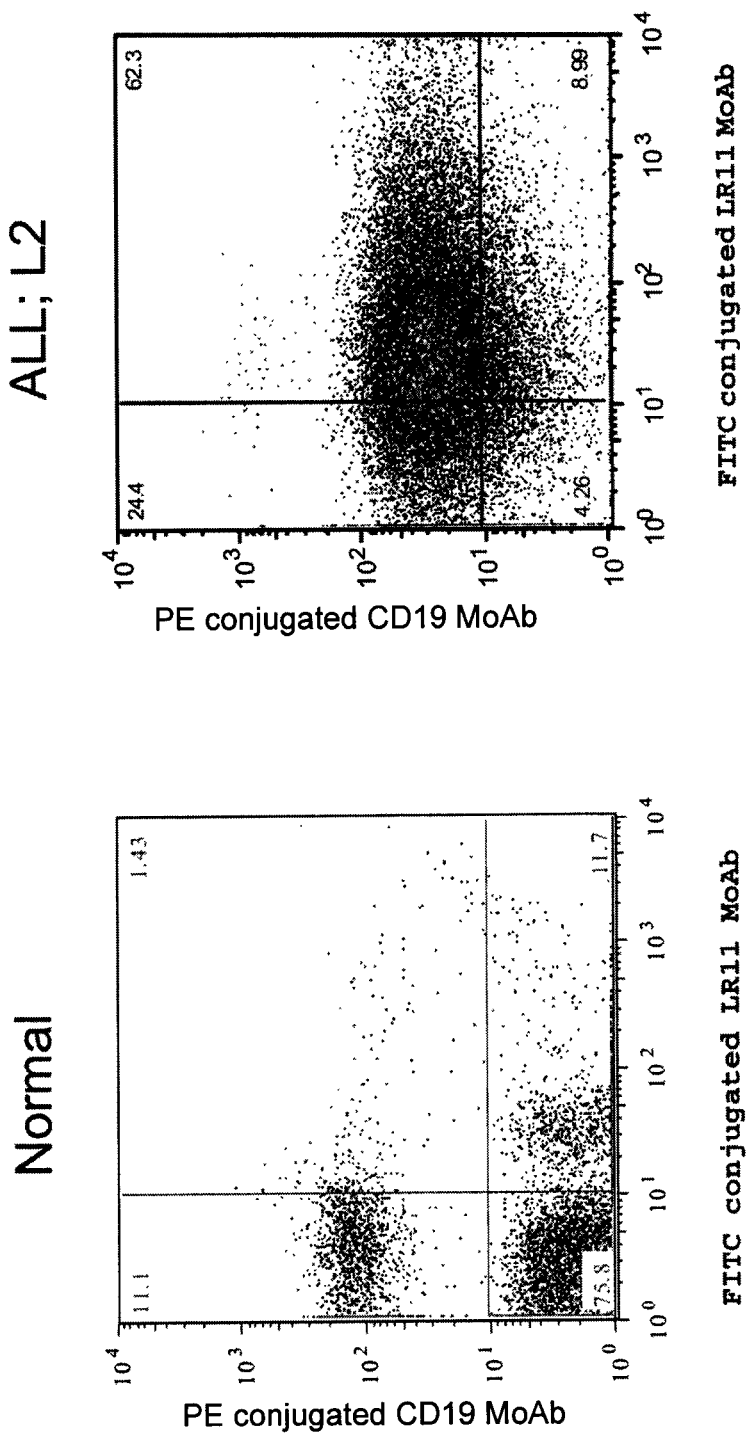
FIG. 4 Graphs showing the results of analysis on the expression of CD19 and LR11 on a cell surface in peripheral blood of a healthy subject and an acute lymphoblastic leukemia patient by flow cytometry.

Example 4: Flow Cytometry of Peripheral Blood of Acute Lymphoblastic Leukemia (ALL) Patient Mononuclear leukocytes were separated from peripheral blood of an acute lymphoblastic leukemia patient (FAB classification: L2) through the use of Ficoll-paque PLUS (manufactured by GE Healthcare), and the presence or absence of expression of LR11 on a cell surface was analyzed by flow cytometry as described in Example 2. Peripheral blood of a healthy subject was used as a negative control. $5\times10^5$ cells of each of the cell lines were floated in a Staining Medium and centrifuged at 1,500 rpm for 5 minutes, and then the supernatant was removed. To the pellet were added 3 µL each of a 1 mg/mL FITC-labeled anti-LR11 monoclonal antibody (M3) and a PE-labeled anti-CD19 antibody (manufactured by BD pharmingen), and the mixture was reacted at 4° C. for 60 minutes. The cells were washed twice with the Staining Medium, and then flow cytometry analysis was carried out through the use of JSAN (manufactured by Bay bioscience) according to the instruction manual. FIG. 4 shows the results.

In leukocytes derived from the peripheral blood of the healthy subject, LR11 was mostly negative in a positive fraction of CD19 as a B cell surface marker. On the other hand, in leukocytes derived from the peripheral blood of the acute lymphoblastic leukemia patient, LR11 was found to be positive in most of lymphoblastic cells which turned into leukemia cells to become CD19-positive.

Figure 5:
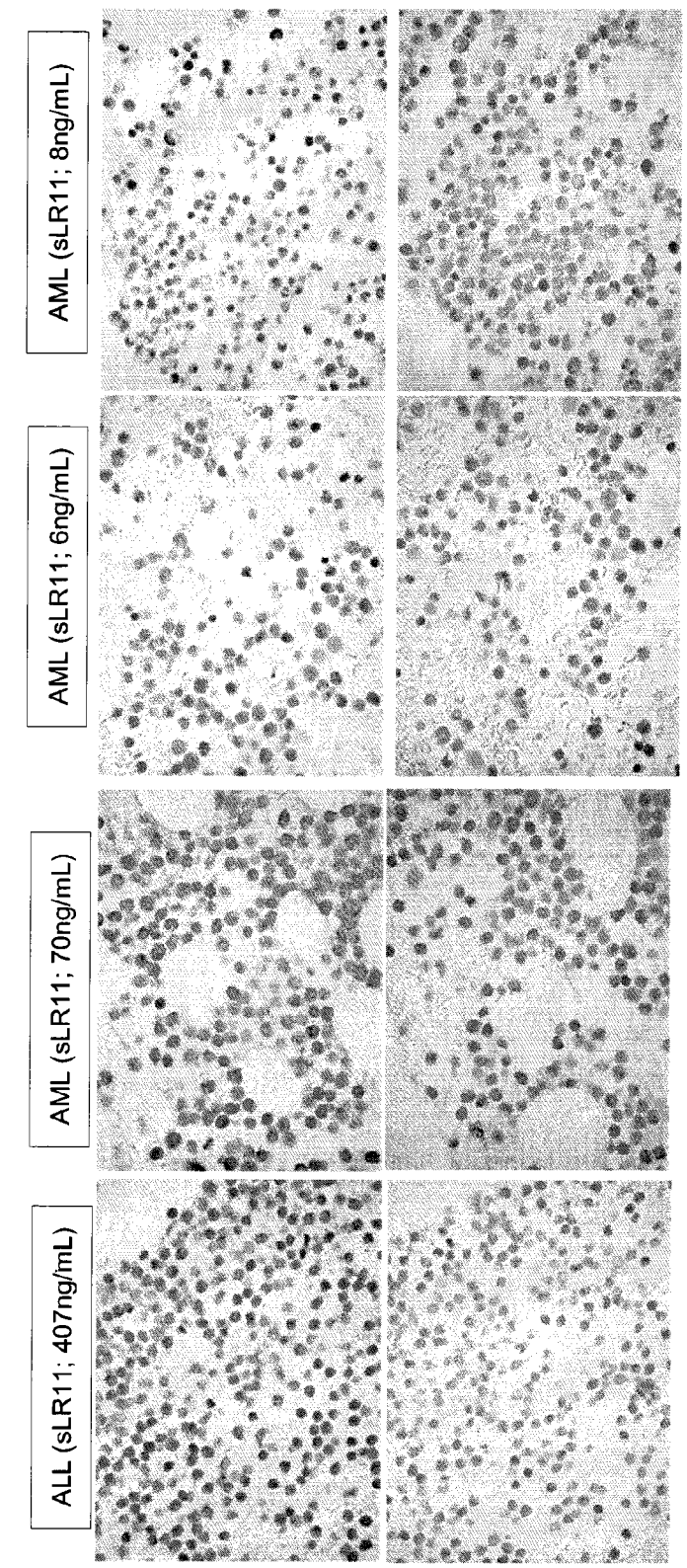
FIG. 5 Images showing the expression of LR11 in an acute leukemia patient-derived bone marrow tissue detected by immunostaining.

Example 5: Immunostaining of Bone Marrow Tissue Derived from Acute Leukemia Patient Bone marrow tissues of one acute lymphoblastic leukemia (ALL) patient (serum soluble LR11 concentration: 407 ng/mL) and three acute myeloid leukemia (AML) patients (serum soluble LR11 concentrations: 70, 6, and 8 ng/mL) were subjected to immunostaining. Normal mouse IgG was used as a negative control. Tissue sections were produced by cutting paraffin-embedded pathological specimens into slices each having a thickness of 4 µm through the use of a microtome. The produced sections were deparaffinized with xylene and subjected to hydration treatment with ethanol, followed by immunostaining according to the following method. A tissue section was immersed in a citrate buffer (pH 6.0) and subjected to microwave treatment to activate an antigen. Next, in order to block endogenous peroxidase, the section was treated with a methanol liquid containing 0.3% hydrogen peroxide for 30 minutes. After that, blocking treatment was performed through the use of Protein Block (manufactured by Dako) and Avidin/biotin blocking kit (manufactured by Vector). Next, a 10 µg/mL anti-LR11 monoclonal antibody (A2-2-3) was applied onto the section, followed by a reaction at 4° C. overnight. The section was washed with TBS (50 mM Tris-HCl and 150 mM NaCl) and then subjected to a reaction with 500-fold diluted biotin-conjugated rabbit anti-mouse IgG (manufactured by Dako) (final concentration: 1.14 ng/mL) at room temperature for 30 minutes. After washing, the section was subjected to a reaction with peroxidase-conjugated streptavidin (manufactured by Nichirei) at room temperature for 5 minutes, washed with TBS, and visualized with a coloring reagent (0.3 mg/mL diaminobenzidine, 0.006% hydrogen peroxide, and 50 mM Tris-HCl (pH 7.6)). Finally, the section was subjected to nuclear staining through the use of Mayer's Hematoxylin (manufactured by Muto), dehydrated by ethanol treatment, and cleared with xylene, and then mounted with Malinol (manufactured by Muto). FIG. 5 shows the results.

The results of immunohistostaining using the anti-LR11 monoclonal antibody (A2-2-3) described in Example 1 gave such an interesting finding that the expression of LR11 was observed in a tissue derived from a patient who had a normal level of serum soluble LR11 as well as a tissue derived from a patient who had a high level of serum soluble LR11. In addition to the expression of LR11 on surfaces of undifferentiated monocytes and B cells in peripheral blood as shown in Examples 3 and 4, it was suggested that detecting the expression of LR11 in a tissue section is applicable to evaluation of the effect of treatment and monitoring of recurrence. Further, a thorough examination using a tumor tissue section is performed in malignant lymphoma or the like, in which cancer cells are generally not detected in peripheral blood, and hence detecting the expression of LR11 in a tissue section for evaluating the effect of treatment and monitoring of recurrence is considered to be valuable.

Example 6: Flow Cytometry of Carcinoma Cell Line

Figure 6:
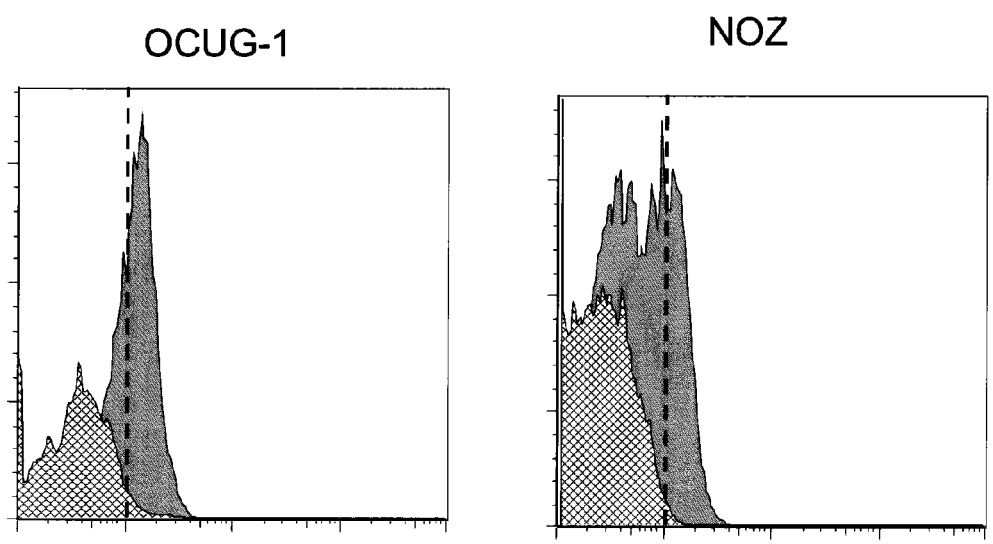
FIG. 6 Graphs showing the results of analysis on the expression of LR11 on a cell surface in a gallbladder cancer-derived cell line by flow cytometry.

As in the carcinomas, serum soluble LR11 was detected at a high concentration in many cases of gallbladder cancer, two kinds of gallbladder cancer-derived cell lines (OCUG-1 and NOZ) were used, and the presence or absence of expression of LR11 on a cell surface was analyzed by flow cytometry as described in Example 2. Cells trypsinized after culture and passed through a nylon mesh were used. $5\times10^5$ cells of each of the cell lines were floated in a Staining Medium and centrifuged at 1,500 rpm for 5 minutes, and then the supernatant was removed. To the pellet were added 3 µL of a 1 mg/mL FITC-labeled anti-LR11 monoclonal antibody (M3), and the mixture was reacted at 4° C. for 60 minutes. The cells were washed twice with the Staining Medium, and then flow cytometry analysis was carried out through the use of JSAN (manufactured by Baybioscience) according to the instruction manual. Normal mouse IgG (manufactured by BD pharmingen) was used as a negative control for the FITC-labeled anti-LR11 monoclonal antibody. As a result, the ratios of LR11-positive cells were about 60% for OCUG-1 and about 20% for NOZ (FIG. 6).

Example 7: Cell Immunity

The NB-4 line, one of the hematopoietic tumor-derived cells, in which LR11 was strongly expressed on a cell surface in the results of Example 5, was proliferated with an HT medium, washed twice with PBS, and then suspended in PBS so that the number of cells was 1 to $2\times10^7$. The suspension was intraperitoneally injected into BALB/c mice (female) to be immunized. The immunization was performed every other week or every week, and the anti-LR11 antibody titer of mouse serum was confirmed at an appropriate timing by the method shown below.

Human urea-derived purified soluble LR11 diluted to 50 ng/mL with PBS was added to a microplate (manufactured by NUNC) at 50 µL per well, and immobilized at room temperature for 2 hours. After washing with PBS containing 0.05% Tween 20 (PBST), PBST containing 1% BSA (BSA-PBST) was added to the microplate at 200 µL per well to perform blocking at room temperature for 1 hour. Blood was collected from the tail of the mice, and the resultant serum was diluted 200 to 1, 600-fold with BSA-PBST and added to the microplate at 50 µL per well, followed by a reaction at room temperature for 1 hour. After washing with PBST, an HRP-labeled anti-mouse IgG polyclonal antibody (Rockland) was diluted 10,000-fold and added to the microplate at 50 µL per well, followed by a reaction at room temperature for 1 hour. After washing with PBST, an o-phenylenediamine substrate liquid was added to the microplate at 50 µL per well, followed by a reaction at room temperature for 20 minutes. The reaction was terminated by adding 1.5 N sulfuric acid to the microplate at 50 μL per well. Then, measurement was performed with a microplate reader (Abs. 492 nm).

Figure 7:
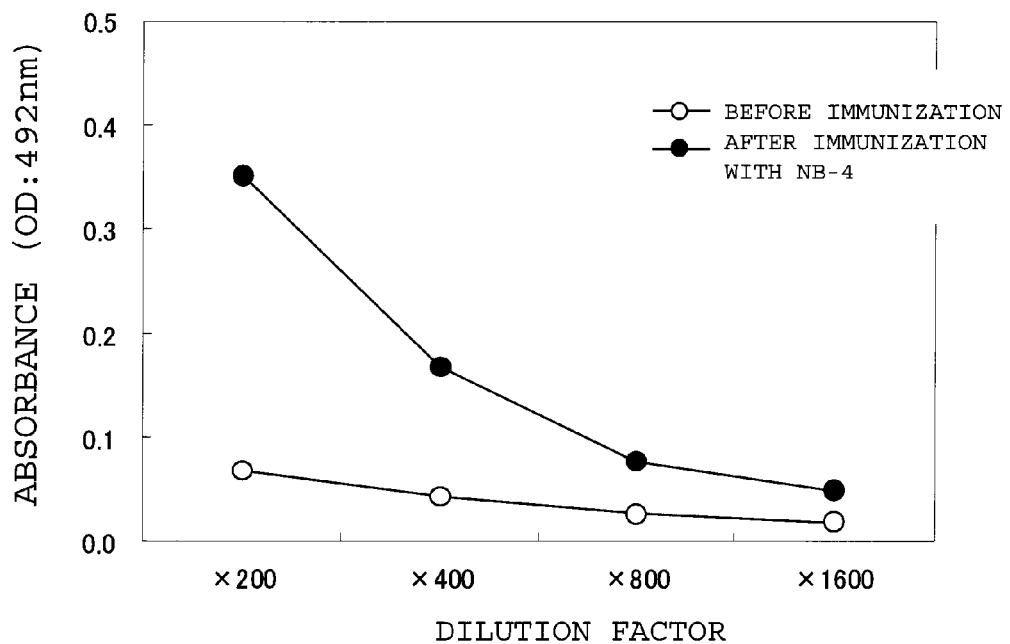
FIG. 7 A graph showing an anti-LR11 antibody titer in mouse serum confirmed through intraperitoneal immunization of mice with an NB-4 cell line.

FIG. 7 shows the results of confirmation of the anti-LR11 antibody titer of mouse serum after five times of immunization.

Almost no reaction with the immobilized human urea-derived purified LR11 was observed in mouse serum before immunization. On the other hand, a clear reaction with the immobilized human urea-derived purified LR11 was observed in the case of the immunization of the NB-4 cell line. The results confirmed that an antibody against LR11 was produced. An antibody binding to LR11 expressed on a malignant tumor cell surface and an antibody having cytotoxicity are obtained by extirpating spleen according to a conventional method at a time when the antibody titer reaches a sufficiently high value, carrying out cell fusion, establishing anti-LR11 monoclonal antibodies, and selecting from the antibodies an antibody having a binding activity to LR11 on a tumor cell surface, and a neutralizing activity on the bioactivity of LR11 and/or a cytotoxicity activity. Further, the cytotoxicity activity may be imparted or enhanced by a known method.

Example 8: Confirmation of LR11 Protein in Various Carcinoma Cell Lines

The expression of an LR11 protein in various epithelial tumor cell lines was confirmed by the western blot method using an anti-LR11 monoclonal antibody (A2-2-3) employed in Example 1. The following cell lines were used: a total of 14 kinds of cell lines including HLE (derived from liver cancer), MKN 1 (derived from stomach cancer), T.Tn (derived from esophageal cancer), COLO201 (derived from large bowel cancer), AsPC-1 (derived from pancreatic cancer), Caki-1 (derived from kidney cancer), Oka-C-1 (derived from lung cancer), PC-3 (derived from prostate cancer), KMBC-2 (derived from bladder cancer), HeLa (derived from cervical cancer), OVISE (derived from ovarian cancer), YMB-1 (derived from breast cancer), KINGS 1 (derived from neurotumor), and G-361 (derived from malignant melanoma). Those cell lines were each suspended in a designated medium (e.g., RPMI-1640 containing 10% fetal bovine serum and penicillin/streptomycin), and cultured and proliferated in a 5% $CO_2$ incubator at 37° C. for an appropriate time. The proliferated cells were washed several times with PBS and then harvested through the use of a trypsin-EDTA solution (manufactured by Invitrogen; 25200-072). The number of cells was counted for each of the cell lines, and the cells were fractionated so that the number of the cells was $1 \times 10^7$. After that, the cells were suspended in an appropriate amount of PBS and collected by centrifugation. This operation was repeated three times to wash the cells. To the collected cells were added 100 μL of PBS containing a 1% protease inhibitor (manufactured by Sigma-Aldrich; P8340). After that, the cells were homogenized with an ultrasonic vibrator (homogenizer). The homogenized fragment of the cells was removed by centrifugation. Then, the supernatant was subjected to ultracentrifugation (100,000 g, 10 minutes) to precipitate a membrane fraction. The supernatant was removed, and the precipitate was washed with PBS. Then, 100 μL of PBS containing a 1% protease inhibitor (manufactured by Sigma-Aldrich; P8340) and 1% MEGA-9 were added, and the membrane fraction was suspended and dissolved with an ultrasonic vibrator (homogenizer). The resultant was subjected to ultracentrifugation (100,000×g, 10 minutes) again to remove an insoluble membrane fraction, to thereby give a solubilized membrane fraction solution.

2 μL per lane of the solubilized membrane fraction solution of each of the cell lines were subjected to boil under a reductive condition containing SDS. The treated liquids were applied to the respective lane of SDS-PAGE (2 to 15%) and separated by electrophoresis. After the completion of the electrophoresis, the proteins were transferred from the gel to a PVDF membrane and subjected to a reaction with the anti-LR11 monoclonal antibody (A2-2-3) as a primary antibody, followed by a reaction with a combination of a biotinylated anti-mouse IgG polyclonal antibody (DAKO) and HRP-labeled streptavidin and finally visualized with diaminobenzidine. Thus, LR11 was detected.

Figure 8:
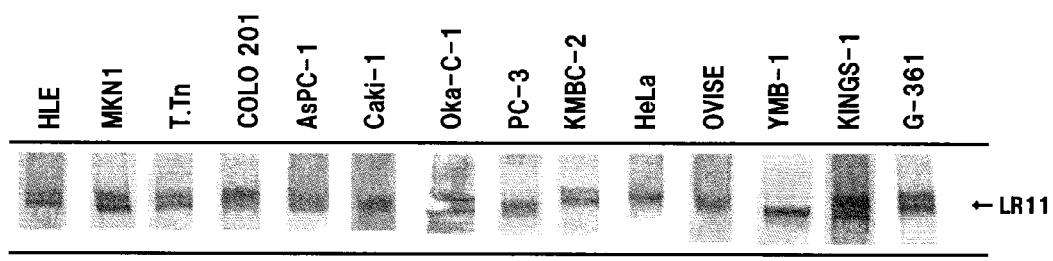
FIG. 8 An image showing the expression of LR11 on a cell surface in various carcinoma cell lines detected by a western blot method through the use of their membrane fraction lysates.

As a result, in the membrane fraction lysates of all the 14 kinds of cell lines used, a band representing the LR11 protein was observed (FIG. 8). This finding suggests that the expression of the LR11 protein may be promoted on a cell surface at a lesion site of a patient with a carcinoma disease.

Example 9: Immunostaining of Malignant Lymphoma Patient-Derived Tissue

Figure 9:
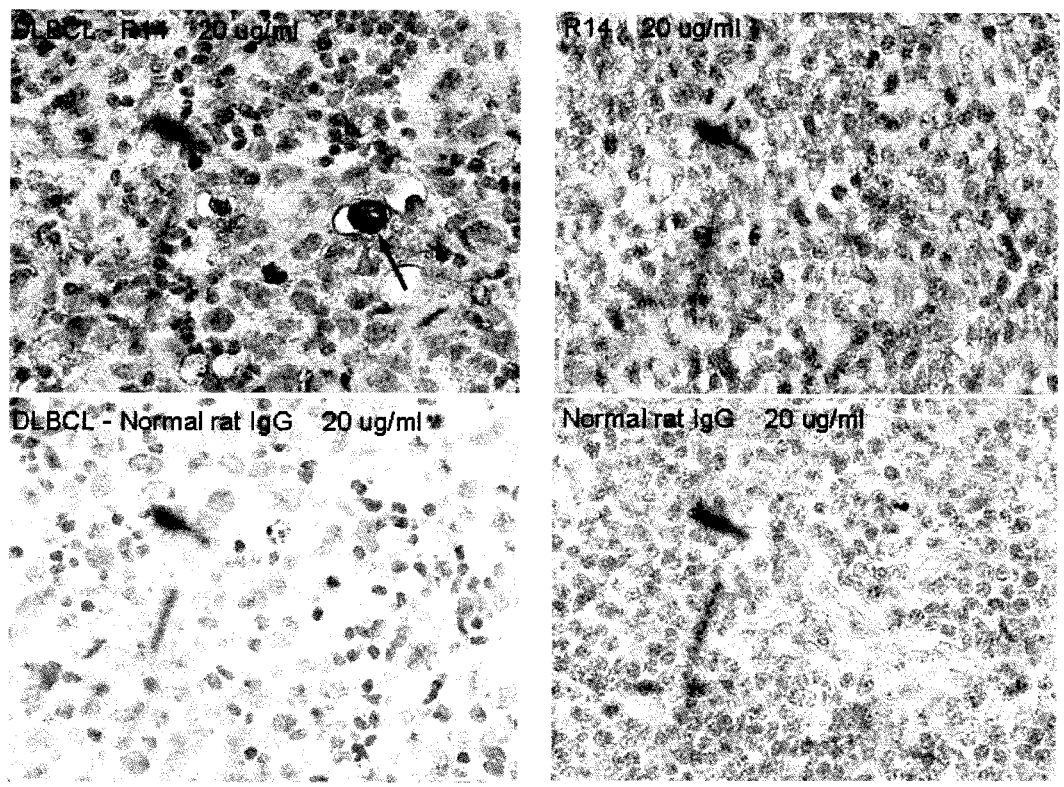
FIG. 9 Images showing the expression of LR11 in a malignant lymphoma patient-derived lymph node tissue detected by immunostaining.

As described in the method of Example 5, lymph node tissues of one patient with diffuse large B-cell lymphoma (DLBCL) classified into non-Hodgkin's lymphoma out of malignant lymphomas (serum soluble LR11 concentration: 79 ng/mL) and a healthy subject were subjected to immunostaining. Normal rat IgG (manufactured by Santa Cruz Biotechnology) was used as a negative control. Tissue sections were produced by cutting paraffin-embedded pathological specimens into slices each having a thickness of 4 μm through the use of a microtome. The produced sections were deparaffinized with xylene and subjected to hydration treatment with ethanol, followed by immunostaining according to the following method. In order to block endogenous peroxidase, a section was treated with a methanol liquid containing 3% hydrogen peroxide for 5 minutes. After that, blocking treatment was performed through the use of Protein Block (manufactured by Dako). Next, a 10 μg/mL anti-LR11 monoclonal antibody (R14; Non Patent Document 4) and normal rat IgG were applied onto the section, followed by a reaction at room temperature overnight. The section was washed with PBS and then subjected to a reaction with 3,000-fold diluted biotin-conjugated rabbit anti-rat IgG (manufactured by Dako) at room temperature for 30 minutes. After washing, the section was subjected to a reaction with peroxidase-conjugated streptavidin (manufactured by Nichirei) at room temperature for 5 minutes, washed with PBS, and subjected to staining through the use of ImmPACT DAB Peroxidase Substrate (manufactured by Vector Laboratories). Finally, the section was subjected to nuclear staining through the use of Mayer's Hematoxylin (manufactured by Muto), dehydrated by ethanol treatment, and cleared with xylene, and then mounted with Malinol (manufactured by Muto). FIG. 9 shows the results.

The results of immunohistostaining using the anti-LR11 monoclonal antibody (R14) confirmed that LR11 was expressed in the malignant lymphoma tissue section as well.

The invention claimed is:

1. A method of detecting a cell of a hematopoietic tumor and treating a subject having the hematopoietic tumor, the method comprising:

measuring LR11 on a cell surface in a sample of a subject to be tested and suspected of the presence of a cell of a hematopoietic tumor by a flow cytometry, immunohistostaining, or western blot method, wherein the measuring of LR11 on the cell surface comprises binding an anti-LR11 monoclonal antibody labeled with a fluorescent dye to LR11 on the cell surface, comparing measurement results of LR11 in the sample with measurement results in a healthy subject group and/or a cancer patient group obtained in advance, thereby detecting the presence of a cell of a hematopoietic tumor in the sample, and treating the subject having the hematopoietic tumor based on results of the comparison.

2. The method of claim 1, wherein the hematopoietic tumor is leukemia or malignant lymphoma.

3. The method of claim 2, wherein the hemopoietic tumor is leukemia, wherein the leukemia is acute leukemia.

4. The method of claim 2, wherein the hematopoietic tumor is malignant lymphoma, wherein the malignant lymphoma is non-Hodgkin's lymphoma.

5. The method of claim 1, wherein the sample to be tested is peripheral blood, a bone marrow aspirate, or a tissue section.

6. The method of claim 1, wherein the sample to be tested is a living-body derived sample.

7. The method of claim 6, wherein the sample is derived from a mammal.

8. The method of claim 7, wherein the mammal is at least one selected from the group consisting of a mouse, a rat, a rabbit, a pig, a dog, a cat, and a human.

9. The method of claim 1, wherein, when the hematopoietic tumor cell is present, a concentration or amount of LR11 on a cell surface in the sample has a higher value, when the severity of a hematopoietic tumor is high or when there is a risk of recurrence, than a measured value for the healthy subject group and/or the cancer patient group.

10. The method of claim 1, wherein the measurement results include the presence and/or quantity of LR11 in the sample, and the comparing comprises comparing the presence and/or quantity of LR11 in the sample to that of the healthy subject group and/or the cancer patient group, and the method further comprises providing a diagnosis based on the comparison of the presence and/or quantity of LR11 in the sample.

11. The method of claim 10, wherein, when the hematopoietic tumor cell is present, a concentration or amount of LR11 on a cell surface in the sample has a higher value, when severity of a hematopoietic tumor is high or when there is a risk of recurrence, than measured values for the healthy subject group and/or the cancer patient group.

12. A method of detecting LR11 in a human patient, the method comprising:

obtaining a living body-derived sample from a human patient;

detecting whether LR11 is present in the living body-derived sample by contacting the living body-derived sample with an anti-LR11 monoclonal antibody labeled with a fluorescent dye and detecting binding between LR11 and the antibody, and measuring LR11 on a cell surface in the living body-derived sample, wherein the living body-derived sample is a sample suspected of the presence of a cell of a hematopoietic tumor.

13. The method of claim 12, further comprising comparing measurement results of LR11 in the living body-derived sample with measurement results in a healthy subject group and/or a cancer patient group obtained in advance, wherein the living body-derived sample is a sample suspected of the presence of a cell of a hematopoietic tumor.

14. The method of claim 13, wherein the comparing comprises comparing the presence and/or quantity of LR11 in the living body-derived sample to that of the healthy subject group and/or the cancer patient group, and the method further comprises providing a diagnosis and a treatment based on the comparison of the presence and/or quantity of LR11 in the living body-derived sample.

15. The method of claim 12, wherein the living body-derived sample is a peripheral blood sample.

16. The method of claim 12, wherein the living body-derived sample is a blood cell sample.

17. The method of claim 16, wherein the blood cell sample is a leukocyte cell sample.

18. The method of claim 16, wherein the blood cell sample is a mononuclear leukocyte sample.

19. A method of detecting LR11 in a human patient, the method comprising:

obtaining a tissue section sample from a human patient;

detecting whether LR11 is present in the sample by contacting the tissue section sample with an anti-LR11 monoclonal antibody labeled with or a fluorescent molecule antibody and detecting binding between LR11 and the antibody, and measuring LR11 on a cell surface in the tissue section sample, wherein the tissue section sample is a sample suspected of the presence of a cell of a hematopoietic tumor.

20. A method of detecting a cell of a hematopoietic tumor and treating a subject having the hematopoietic tumor, the method comprising:

measuring LR11 on a cell surface in a sample of a subject to be tested and suspected of the presence of a cell of a hematopoietic tumor by a flow cytometry, immunohistostaining, or western blot method, wherein the measuring of LR11 on the cell surface comprises binding an anti-LR11 monoclonal antibody labeled with a biotin-conjugated secondary antibody to LR11 on the cell surface, comparing measurement results of LR11 in the sample with measurement results in a healthy subject group obtained in advance, thereby detecting the presence of a cell of a hematopoietic tumor in the sample, and treating the subject having the hematopoietic tumor based on results of the comparison.

21. A method of detecting LR11 in a human patient, the method comprising:

obtaining a living body-derived sample from a human patient;

detecting whether LR11 is present in the living body-derived sample by contacting the living body-derived sample with an anti-LR11 monoclonal antibody labeled with a biotin-conjugated secondary antibody and detecting binding between LR11 and the antibody, and measuring LR11 on a cell surface in the living body-derived sample, wherein the living body-derived sample is a sample suspected of the presence of a cell of a hematopoietic tumor.

22. A method of detecting LR11 in a human patient, the method comprising:

obtaining a tissue section sample from a human patient;

detecting whether LR11 is present in the sample by contacting the tissue section sample with an anti-LR11 monoclonal antibody labeled with a biotin-conjugated secondary antibody and detecting binding between LR11 and the antibody, and measuring LR11 on a cell surface in the tissue section sample,
wherein the tissue section sample is a sample suspected of the presence of a cell of a hematopoietic tumor.

* * * * *